United States Patent [19]

Hung

[11] 4,286,571
[45] Sep. 1, 1981

[54] KENSHIN HEATING INSTRUMENT

[76] Inventor: David P. J. Hung, 229-03 64th Ave., Bayside, N.Y. 11364

[21] Appl. No.: 128,432

[22] Filed: Mar. 10, 1980

[51] Int. Cl.$^3$ .............................................. A61F 7/08
[52] U.S. Cl. .................................................. 126/206
[58] Field of Search .................. 126/206, 204; 43/23; 220/8, 206; 138/108, 113; 206/537; 16/110.5

[56] References Cited

U.S. PATENT DOCUMENTS

| | | | |
|---|---|---|---|
| 692,168 | 1/1902 | Snyder | 126/206 |
| 835,150 | 11/1906 | Bowditch | 126/206 |
| 1,475,163 | 11/1923 | Allport | 126/206 |
| 3,858,567 | 1/1975 | Slogaski | 126/206 |
| 4,020,825 | 5/1977 | Fusetti | 126/206 |

FOREIGN PATENT DOCUMENTS

| | | | |
|---|---|---|---|
| 66836 | 1/1914 | Switzerland | 126/206 |
| 25347 | 10/1897 | United Kingdom | 126/206 |

Primary Examiner—Samuel Scott
Assistant Examiner—Randall L. Green
Attorney, Agent, or Firm—Allison C. Collard; Thomas M. Galgano

[57] ABSTRACT

A hand-held, non-electrically powered heating instrument includes a generally cylindrical, hollow, elongated, metallic first element having means for mounting a charge of burnable fuel therein and also having a plurality of air vents at one end thereof and an air inlet opening at the opposite end thereof. The instrument also includes a generally cylindrical, hollow, elongated, metallic second element having a substantially closed end and an opposite open end and a plurality of air vents formed substantially adjacent to the closed end thereof. The second element is configured and dimensioned to permit the first element to be releasably and telescopically received therein through the open end thereof, so that the air vents of both elements may communicate with one another. The first and second elements are slidable relative to one another in both a rotatably and longitudinal manner so as to permit regulation of the amount of air flowing through the air inlet opening and through the vents.

9 Claims, 5 Drawing Figures

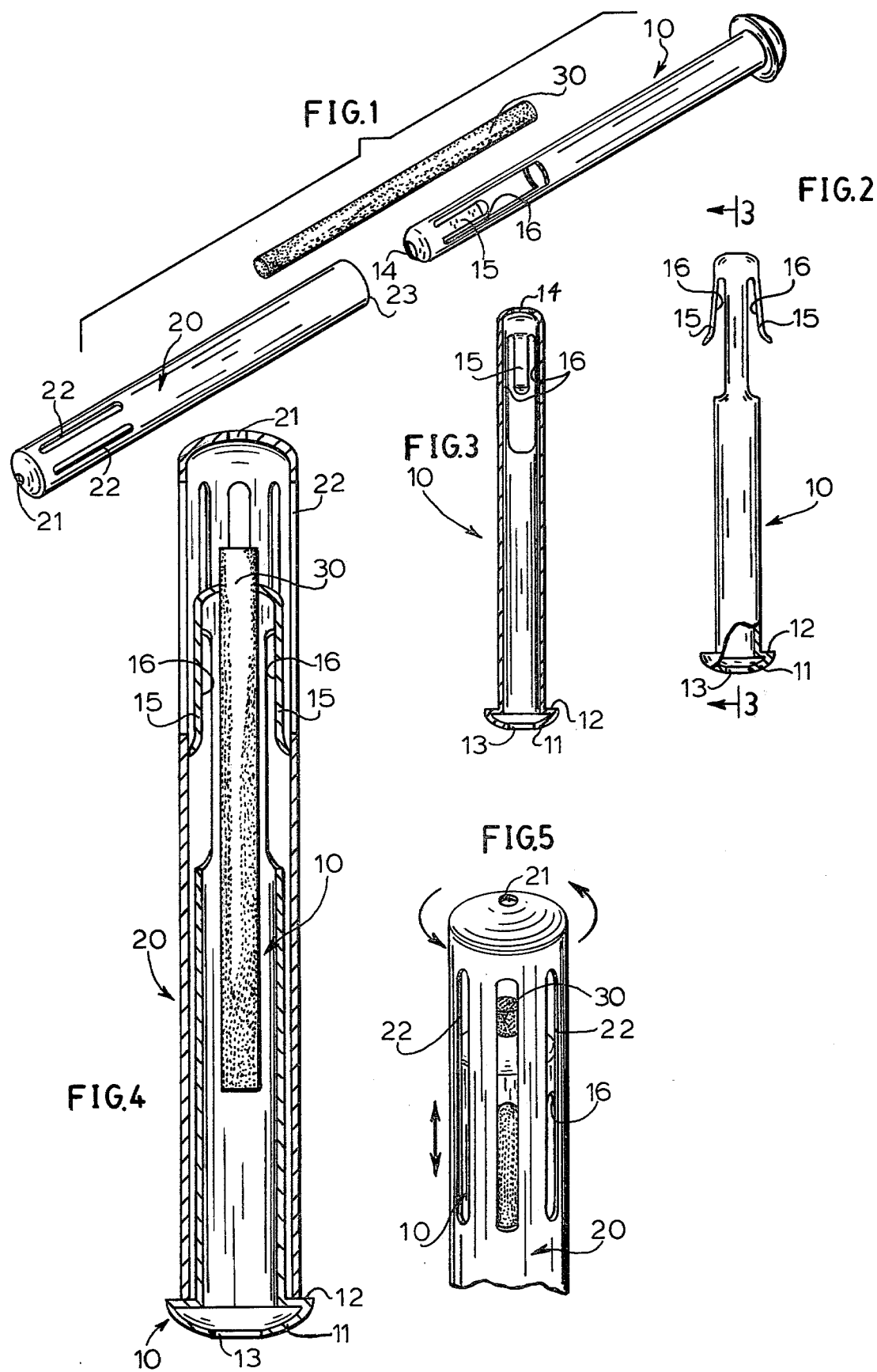

KENSHIN HEATING INSTRUMENT

The present invention relates to a heating instrument. More particularly, it relates to a hand-held, non-electrically powered heating instrument which may be used to provide external warmth, comfort, and relaxation.

Various types of heating instruments, and, in particular, hand-held, fuel-burning heating instruments are well-known in the art (e.g., U.S. Pat. Nos. 692,168; 1,015,661; 1,475,163; 3,858,567; 4,020,825). While these prior art constructions are perhaps generally satisfactory, for the most part, they each have certain drawbacks. For example, some require rather complicated and cumbersome constructions. Others do not afford effective air flow regulation. In addition, some are inconvenient to operate and handle and not totally effective.

It is therefore an object of the present invention to afford a novel heating instrument which may be hand-held, is non-electrically powered, and which is simple and facile to use.

It is a further object of the invention to afford a novel hand-held heating instrument which is of simple construction, is reliable in operation, and is economical to manufacture.

It is a more particular object of the invention to provide such a novel hand-held heating instrument having the foregoing attributes and characteristics, which is light and provides external warmth, comfort and relaxation.

Certain of the foregoing and related objects are readily attained in a hand-held, non-electrically powered heating instrument which includes a generally cylindrical, hollow, elongated, metallic first element having means for mounting a charge of burnable fuel therein and also having a plurality of air vents at one end thereof and an air inlet opening at the opposite end thereof. The heating instrument also includes a generally cylindrical, hollow, elongated, metallic second element having a substantially closed end and an opposite open end and a plurality of air vents formed substantially adjacent to said closed end thereof. The second element is configured and dimensioned to permit the first element to be releasably and telescopically received therein through the open end thereof, so that the air vents of both elements may communicate with one another. The first and second elements are slidable relative to one another in both a rotatable and longitudinal manner so as to permit regulation of the amount of air flowing through the air inlet opening and through the vents.

Most desirably, the heating instrument also includes a charge of burnable fuel, such as a stick of incense. In addition, it is also preferable that the first and second elements are made from silver-coated brass.

In a preferred embodiment of the invention, the first element has a knob-like end segment formed on the opposite end thereof in which the air inlet opening is formed which serves as a finger grip to permit facile sliding movement of the first element relative to the second element. Most advantageously, the first element has a pair of opposed radially outwardly-extending resilient flanges disposed adjacent to the one end thereof which serve to enhance frictional engagement between the first and second elements during telescopic engagement therebetween. It is also desirable that the first element be provided with an opening extending through the one end thereof in which the charge of fuel may be mounted.

In a particularly preferred embodiment, the plurality of air vents formed in the second element comprise a plurality of parallel and radially spaced-apart elongated slots formed in the second element adjacent to the closed end thereof, the latter of which desirably has an air outlet opening extending therethrough. The plurality of air vents of the first element also advantageously comprise a plurality of parallel and radially spaced-apart elongated slots formed in the first element on the opposite lateral sides of the flanges.

Other objects and features of the present invention will become apparent from the following detailed description, considered in connection with the accompanying drawing, which discloses a single embodiment of the invention. It is to be understood, however, that the drawing is designed for the purpose of illustration only, and not as a definition of the limits of the invention.

In the drawing, wherein similar reference characters denote similar elements throughout the several views:

FIG. 1 is a perspective view of the heating instrument embodying the present invention which comprises an inner cylindrical element, an outer cylindrical element, and a stick of solid fuel, shown in a disassembled state;

FIG. 2 is a side elevational view, in part section, of the inner cylindrical element;

FIG. 3 is a cross-sectional view taken along line 3—3 of FIG. 2;

FIG. 4 is an enlarged cross-sectional view, in part elevation, of the heating instrument, shown in an assembled state; and FIG. 5 is an enlarged, fragmentarily-illustrated perspective view of the top portion of the heating instrument, further illustrating the relative rotational and longitudinal displacement possible between the inner and outer cylindrical elements.

Turning now in detail to the appended drawing, therein illustrated is a novel hand-held, non-electrically powered, fuel burning heating instrument which includes a generally cylindrical, elongated, metallic, hollow first element 10, a generally cylindrical, elongated, metallic, hollow second element 20, and a stick of solid fuel 30 which may comprise, e.g., a stick of incense, a wick, etc.

As can be seen more clearly in FIGS. 2 and 3, first element 10 has a knob-like end segment 11 of generally semi-elliptical cross-section which defines an abutment shoulder 12 and which has an air inlet opening 13 extending therethrough. At the opposite end of first element 10, a mounting aperture 14 is provided for the solid stick of fuel 30. Adjacent to mounting aperture 14 are a pair of opposed, resilient, radially outwardly-extending flanges 15, the purpose for which will be described in greater detail hereinafter. Flanges 15 are each flanked by a pair of elongated radially spaced-apart slots 16 which serve as air vents; the pair of slots 16 disposed on opposite sides of the same flange 15 merging into one another underneath the tip of the respective flange 15, so as to facilitate easy construction of flange 15, as well as to provide a greater venting area, if needed.

First element 10 is dimensioned so that it may be telescopically received within second element 20, as shown in FIG. 4. Element 20 has a substantially closed top end through which an air outlet opening 21 extends, and an opposite open end 23 in which first element 10 is inserted. Second element 20 is provided with a plurality of radially spaced-apart and parallel, elongated slots 22, adjacent to the top end thereof, which serve as air vents.

As shown in FIGS. 4 and 5, when first element 10 is telescopically received within second element 20, the respective air vents 16 and 22 may be at least partially alignable with one another so as to define an air flow through elements 10 and 20. The amount of communication between the vents may be changed by rotational or longitudinal displacement of the first element 10 and the second element 20 relative to one another, as shown in FIG. 5. To facilitate maintenance of the desired relative position of elements 10 and 20, flanges 15, as shown in FIG. 4, provide frictional engagement between first element 10 and second element 20 so as to restrict unintentional relative movement therebetween. In addition, abutment shoulder 12, of course, limits the depth of insertion of first element 10 in second element 20, due to its eventual abutment with the rim of open end 23.

Turning now to the operation of the device, initially the stick of solid fuel 30 is mounted in mounting aperture 14 of first element 10, as shown in FIGS. 4 and 5. Then the tip of the stick of solid fuel 30 would be ignited and allowed to burn down a bit, at which point the frame would be put out, although the stick would still be burning or smoldering. First element 10 would then be inserted into the open end 23 of the second element 20 and the positioning of the respective air vents or slots 16 and 22 of each element would be appropriately adjusted by suitable rotational and longitudinal sliding movement of elements 10 and 20 to either enlarge or decrease the area for air discharge through vents 22; the air initially being supplied through air inlet opening 13 into the interior of element 10, following which it exits through vents 16 and finally vents 22. The knob-like end segment 13 facilitates this relative movement, since it serves as a finger grip.

After the proper amount of air flow is adjusted to effect continued burning of the stick of solid fuel 30 at a moderate rate, the heating unit would then be lightly passed over the skin for a period of maybe ten minutes or more moving it back and forth without stopping. In particular, it may be conveniently rolled between the palms of the user's hand. Aside from the obvious external warmth and comfort it provides, it also affords a measure of mental relaxation as a result of this rhythmic movement of the heating instrument.

Various changes and modifications can of course be made in this heating instrument, as will be obvious to those skilled in the art. For instance, although it is preferable that the first and second elements comprise brass cylinders which may be coated with a precious metal, such as silver, other heat conducting materials may, of course, be used. In addition, although the particular positioning and configuration of the air vents and air inlets and outlets as well as the configuration of the elements themselves, has been found to be particularly effective, it may be possible to modify the same as long as the essential parameters, e.g., regulation of air flow, are maintained in any design changes.

Thus, while only one embodiment of the present invention has been shown and described, it will be obvious that many modifications and changes may be made thereunto, without departing from the spirit and scope of the invention.

What is claimed is:

1. A hand-held, non-electrically powered heating instrument, comprising:
    a generally cylindrical, hollow, elongated, metallic first element having means for mounting a charge of burnable fuel therein and also having a plurality of air vents at one end thereof and an air inlet opening at the opposite end thereof;
    a generally cylindrical, hollow, elongated, metallic second element having a substantially closed end and an opposite open end and a plurality of air vents formed substantially adjacent to said closed end thereof, said second element being configured and dimensioned to permit said first element to be releasably and telescopically received therein through said open end thereof, so that said air vents of both elements may communicate with one another, said first and second elements being slidable relative to one another in both a rotatable and longitudinal manner so as to permit regulation of the amount of air flowing through said air inlet opening and through said vents.

2. The heating instrument according to claim 1, additionally including a charge of burnable fuel.

3. The heating instrument according to claim 2, wherein said charge comprises a stick of incense.

4. The heating instrument according to claim 1, wherein said first element has a knob-like end segment formed on said opposite end thereof in which said air inlet opening is formed which serves as a finger grip to permit facile sliding movement of said first element relative to said second element.

5. The heating element according to claim 4, wherein said first element has a pair of opposed radially outwardly-extending resilient flanges disposed adjacent to said one end thereof which serve to enhance frictional engagement between said first and second elements during telescopic engagement therebetween.

6. The heating element according to claim 1, wherein said plurality of air vents formed in said second element comprises a plurality of parallel and radially spaced-apart elongated slots formed in said second element adjacent to said closed end thereof and wherein said closed end has an air outlet opening extending therethrough.

7. The heating element according to claim 1, wherein said first element has an opening extending through said one end thereof which serves as said mounting means and in which said charge of fuel may be mounted.

8. The heating element according to claim 5, wherein said plurality of air vents of said first element comprise a plurality of parallel and radially spaced-apart elongated slots formed in said first element on the opposite lateral sides of said flanges.

9. The heating element according to claim 1, wherein said elements are made from silver-coated brass.

* * * * *